United States Patent [19]

Bierbaum

[11] Patent Number: 5,464,350
[45] Date of Patent: Nov. 7, 1995

[54] DENTAL HANDPIECE WITH A CHECK VALVE

[75] Inventor: Thomas Bierbaum, Lorsch, Germany

[73] Assignee: Siemens Aktiengesellschaft, Munich, Germany

[21] Appl. No.: 293,437

[22] Filed: Aug. 19, 1994

[30] Foreign Application Priority Data

Aug. 23, 1993 [DE] Germany .................. 9312611 U

[51] Int. Cl.⁶ ........................................ A61C 1/10
[52] U.S. Cl. ............................... 433/84; 433/114
[58] Field of Search ................ 433/132, 91, 114, 433/115, 82, 126, 84; 415/904

[56] References Cited

U.S. PATENT DOCUMENTS 4,607,627 8/1986 Leber et al. .................. 128/66

FOREIGN PATENT DOCUMENTS 271597 6/1988 European Pat. Off. .......... 433/114
4141161 5/1992 Japan .......................... 433/114
6098898 4/1994 Japan .......................... 433/132
8101364 5/1981 WIPO ........................... 433/82

OTHER PUBLICATIONS

Abstract of Japanese Published Application No. 4 307 057 (Oct. 29, 1992) *Patent Abstracts of Japan*, vol. 17, No. 131 (C–1036) 18 Mar. 1993.

*Primary Examiner*—Cary E. O'Connor
*Attorney, Agent, or Firm*—Hill, Steadman & Simpson

[57] ABSTRACT

A dental handpiece has a coupling member in which a passage for delivering a coolant to a discharge nozzle at the head part is provided. In order to prevent a flow-back of contaminated fluid with bacteria past the handpiece, a check valve is provided and comprises a check valve member disposed in a recess that extends radially inward from an outer surface of the coupling member and receives a flexible portion for closing a portion of the passage. The flexible portion is such that when the fluid is turned off, a suction in the fluid line will cause the flexible member to be pressed against the base of the recess and to prevent dripping from the exit nozzle.

15 Claims, 2 Drawing Sheets

DENTAL HANDPIECE WITH A CHECK VALVE

BACKGROUND OF THE INVENTION

The present invention is directed to a dental handpiece which contains a coupling member in which a duct for delivery of a coolant to a discharge nozzle at the head end of the handpiece is arranged, the handpiece includes a check valve that will close or release the duct dependent on the fluid pressure in the duct.

European Patent 0 271 597 discloses a handpiece which has a check valve. The check valve serves the purpose of preventing the liquid from flowing back into the delivery paths after the liquid is shut off and thereby prevents bacteria picked up from the treatment region or oral cavity from proceeding into the apparatus region, which cannot be sterilized after a treatment. In this known handpiece, the check valve is arranged in the region of the head housing of the handpiece. In order to remove the valve member from the duct, a screw cover on the head housing must be removed and then the drive unit arranged in the head housing must also be removed to provide space for removing the valve member.

As already addressed at the onset, the valve serves the purpose of preventing a return flow of the liquid charged with bacteria after the flow of liquid has been shut off externally from the handpiece. The intentional back-absorption or suction for avoiding the formation of droplets at the exit location of the nozzle is not achieved with this type of valve structure.

SUMMARY OF THE INVENTION

The object of the present invention is to provide a cost-beneficial solution that is simple in terms of assembly, with which the formation of droplets at the exit opening of the nozzle can be avoided and also the penetration of bacteria into parts of the handpiece side, including the supply hose, that are connected to the handpiece can be avoided.

In order to accomplish these goals, the present invention utilizes a dental handpiece comprising a head part with an exit nozzle at one end and a coupling member spaced from the head part for coupling the handpiece to a supply source for delivering a cooling fluid to said head part. The coupling member has an outer surface, an inner surface and a passageway for delivering a cooling fluid from the inner surface of the coupling member toward the exit nozzle. The passageway includes a recess with a base wall extending radially inward from the outer surface of the coupling member, a first duct extending from the base wall of the recess to the inner surface of the coupling member and a second duct extending from the recess at a point spaced from the base wall toward the exit nozzle. A check valve member is disposed in the recess and has a movable section forming a closing member for the first duct and an immovable section for sealing the recess adjacent the outer surface of the coupling member.

Other advantages and features of the invention will be readily apparent from the following description of the preferred embodiments, the drawings and claims.

DESCRIPTION OF THE PREFERRED EMBODIMENTS

Figure 1:
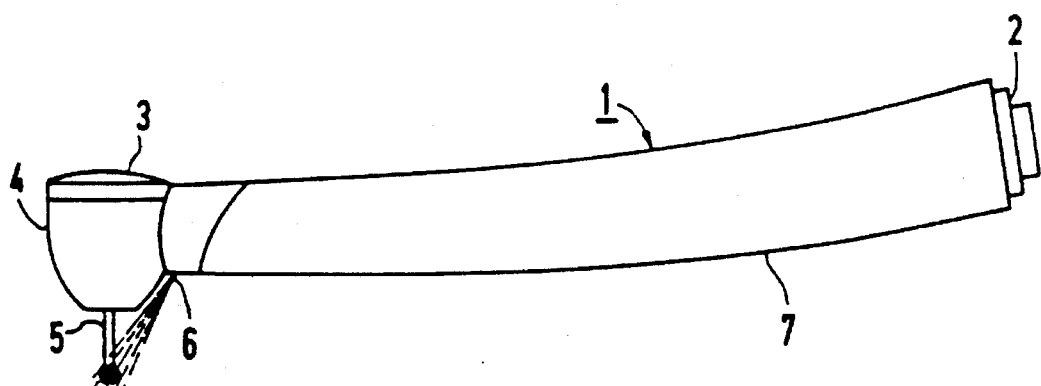
FIG. 1 is a side view of a dental handpiece in accordance with the present invention.
Figure 2:
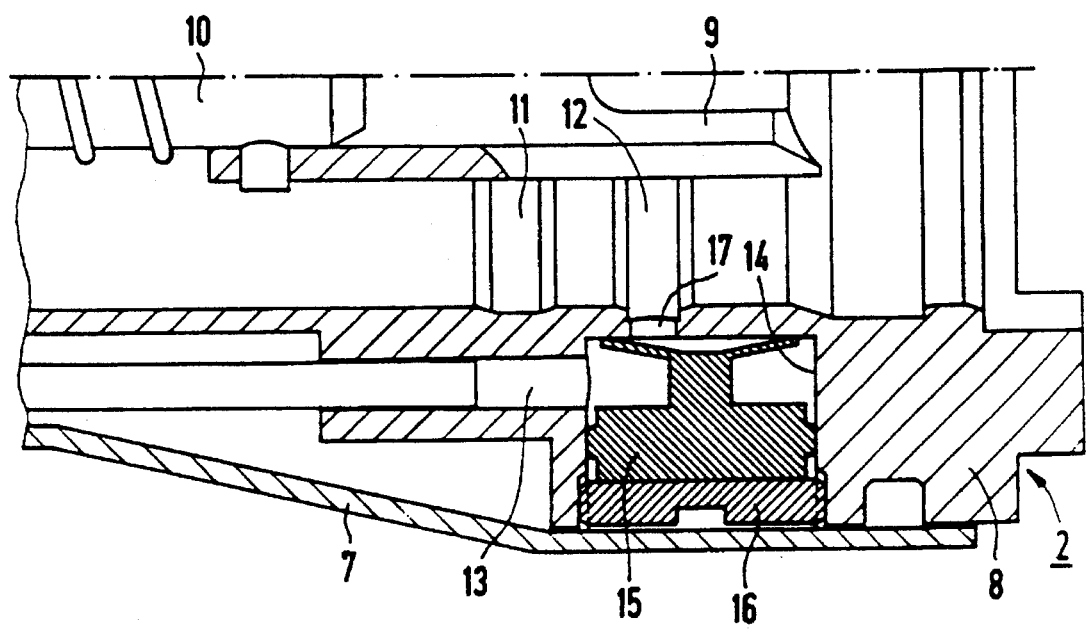
FIG. 2 is an enlarged partial transverse cross sectional view of the dental handpiece illustrating a coupling member having the check valve of the present invention.

The principles of the present invention are particularly useful when incorporated in a dental handpiece, generally indicated at 1 in FIG. 1, which is illustrated as a grip sleeve on whose one end is a connecting fitting 2 for connecting to supply hoses and on the other end is provided with a head part 3. In the head part 3 is a head housing 4 which, in a known way, supports a tool 5 for rotation. Adjacent the head housing 4, an exit nozzle 6 for a fluid coolant, usually cooling water or a mixture of water and air with which the tip of the tool 5 or, respectively, a preparation location can be cooled, is provided. A grip piece 1 has an outer sleeve 7 which extends from the head part 3 to the connecting fitting 2 and surrounds a coupling member 8 illustrated in FIG. 2.

In the present case, the coupling member 8 is fashioned for the acceptance of a peg-shaped connecting part of a drive motor which will have a member for engaging a coupling element 9, which is in the center and transmits torque through a drive shaft section 10 to the head housing 3. The member or part 8, on an inner surface, is provided with annular channels 11 and 12 which form a connection with the connecting part for air and water which are conducted from the connecting part (not shown) of the drive motor to an exit nozzle 6. The annular channel 12, through which water is delivered, discharges through a first duct 17 into a recess 14 which extends radially inward from an outer surface of the member 8. A second duct 13 extends from a point, such as a side wall of the recess 14, toward the exit nozzle 6 which, as illustrated, receives a tube or conduit. A check valve member 15 is introduced into the recess 14. A set screw 16, which is threaded into threads in the recess 14 and sets a prestress of the valve member, fixes the check valve member in the recess. As illustrated, the outer limitation of the recess are covered by the outer sleeve 7 of the gripping member, and this has the advantage that the valve is easily accessible after removing the sleeve 7 or after withdrawing the coupling member 8 therefrom.

Figure 3:
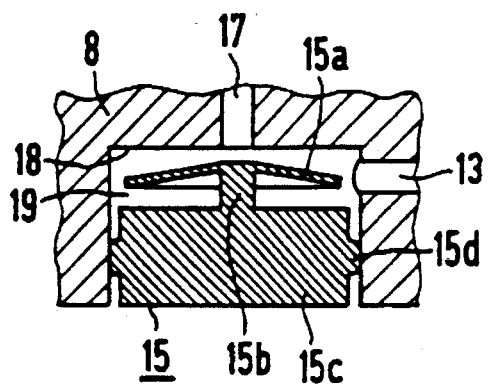
FIG. 3 is an enlarged cross sectional view similar to FIG. 2 illustrating the check valve in an opened position.
Figure 4:
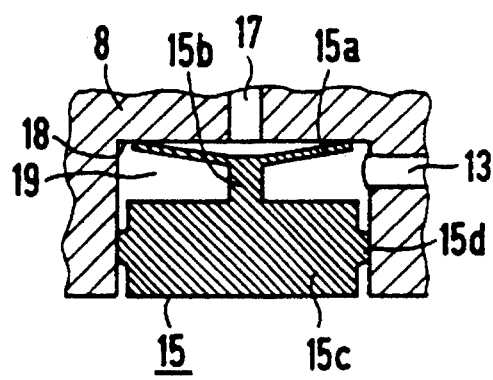
FIG. 4 is an enlarged partial cross sectional view similar to FIG. 2 illustrating the check valve in a closed position.
Figure 5:
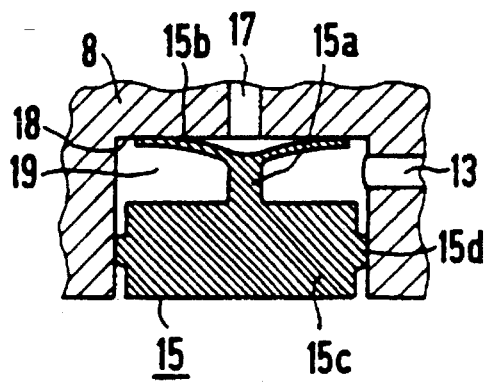
FIG. 5 is a partial cross sectional view illustrating the check valve after the flow of fluid has been shut off.

As best shown in FIGS. 3–5, the check valve member 15 contains an elastic section 15a fashioned in a plate-like shape, which will form a closing member. The valve member 15 also contains an immobile section or base 15c which is connected by a thin web 15b to the elastic section 15a and, thus, provides a chamber 19 between the base 15c and section 15a. To form a seal with the walls of the recess, the immobile or base section 15c has an annular ring or ridge 15d. The valve member 15 is shown in three positions in FIGS. 3–5, with FIG. 3 showing the check valve in an opened position; FIG. 4 showing it in an unloaded, closed position; and FIG. 5 showing it in a condition of backabsorption after delivery of a liquid is shut off. The edges of the section 15a will press only lightly, but in a sealing fashion, against the base 18 to surround the first duct or orifice 17 when in the unloaded, closed position, as illustrated in FIG. 4. The elasticity of the section 15a is such that after the delivery of the flow of liquid is shut off, not only the edge of the plate will press against the base or limiting surface 18, but, as a consequence of a slight back-absorption or suction formed in the delivery line, will press the closing member against the base or limiting surface 18, as illustrated in FIG. 5. This pronounced conforming of the closing member leads to an increase in the volume of the chamber 19 and, as a result thereof, a slight, defined back-suction is applied to the second duct 13 and prevents the formation of droplets at the exit nozzle 6. During the operation, the sealing edge lifts off from the back surface 18, due to the pressure applied through the first duct 17 and will, thus, release the flow.

Special advantages of the handpiece of the invention are that prevention of the back-absorption is present directly in the handpiece and, therefore, assures that the water contaminated with bacteria cannot proceed through the handpiece into the supply hose and, thus, into the supply at the apparatus side. The quantity absorbed back into the handpiece is relatively small and is not dependent on the apparatus. Preferably, the single-piece fashioning of the valve assures a reliable function and easy replacement. Thus, the valve limits the penetration of bacteria to only those regions of the grip piece which can be easily sanitized and prevents the penetration of any bacteria into those portions of a handpiece or apparatus which are difficult to clean and sanitize.

Although various minor modifications may be suggested by those versed in the art, it should be understood that I wish to embody within the scope of the patent granted hereon all such modifications as reasonably and properly come within the scope of my contribution to the art.

I claim:

1. A dental handpiece comprising a head part with an exit nozzle at one end; a coupling member spaced from the head part for coupling the handpiece to a supply source for delivering a cooling fluid to said head part, said coupling member having an outer surface, an inner surface and a passageway for delivery of a cooling fluid from the inner surface to the exit nozzle, said passageway including a recess with a base wall extending radially inward from the outer surface of the coupling member, a first duct extending from the base wall of the recess to the inner surface and a second duct extending from the recess at a point spaced from the base wall toward the exit nozzle; and a check valve member being disposed in the recess having a movable section forming a closing member for the first duct and an immovable section for sealing the recess adjacent to the outer surface of the coupling member.

2. A dental handpiece according to claim 1, wherein the movable section is connected by a center web to the immovable section, said immovable section includes an integral annular sealing element for sealing the chamber relative to a peripheral opening of the recess.

3. A dental handpiece according to claim 2, wherein the check valve member is composed of a one-piece structural part.

4. A dental handpiece according to claim 3, which includes an adjustment element for adjusting a prestress force on the check valve member, said adjustment member being threadably received in said recess.

5. A dental handpiece according to claim 4, wherein the handpiece includes an outside sleeve covering the recess of the coupling member.

6. A dental handpiece according to claim 1, wherein the movable section forming the closing member and the immovable section define a chamber within the recess, said chamber being in communication with the second duct leading to the exit nozzle.

7. A dental handpiece according to claim 6, wherein the movable section is constructed plate-shaped and is composed of an elastic material with a shape and elasticity being selected so that in an unloaded condition, the edges of the movable section will press against the bottom wall of the recess to surround the first duct and when the flow of liquid in the delivery line is shut off, the plate-shaped movable member presses against the bottom wall with a far larger area due to a back-absorption and suction effect occurring in the delivery line.

8. A dental handpiece according to claim 7, wherein the plate-shaped section is connected by a center web to the immovable section and the immovable section includes an annular ridge forming a seal element for sealing the valve member in said recess.

9. A dental handpiece according to claim 8, wherein the check valve member is composed of a one-piece structural part.

10. A dental handpiece according to claim 9, which includes an adjustment element threadably received in the recess for applying a prestress force on the closing member of the check valve member.

11. A dental handpiece according to claim 10, which includes an outer sleeve for receiving the coupling member and covering the recess.

12. A dental handpiece according to claim 7, which includes the recess being provided with threads adjacent the outside surface, and includes an adjustment element threaded in said threads of the recess to adjust the prestress force on the plate-shaped movable section.

13. A dental handpiece according to claim 12, which includes an outer sleeve, said sleeve receiving the coupling member and covering the recess with the adjustment element.

14. A dental handpiece according to claim 1, which includes a threaded element received in threads provided in the recess adjacent the outer surface of the coupling member, said threaded element adjusting the prestressed force on the movable section forming the closing member.

15. A dental handpiece according to claim 1, which includes a sleeve receiving the coupling member and covering the recess with the check valve member.

\* \* \* \* \*